United States Patent
Li et al.

(10) Patent No.: US 11,510,574 B2
(45) Date of Patent: Nov. 29, 2022

(54) THREE-DIMENSIONAL (3D) OPTICAL COHERENCE TOMOGRAPHY ANGIOGRAPHY (OCTA) METHOD AND SYSTEM BASED ON FEATURE SPACE

(71) Applicant: ZHEJIANG UNIVERSITY, Hangzhou (CN)

(72) Inventors: Peng Li, Hangzhou (CN); Luzhe Huang, Hangzhou (CN); Yiming Fu, Hangzhou (CN)

(73) Assignee: ZHEJIANG UNIVERSITY, Hangzhou (CN)

(*) Notice: Subject to any disclaimer, the term of this patent is extended or adjusted under 35 U.S.C. 154(b) by 0 days.

(21) Appl. No.: 17/628,579

(22) PCT Filed: Apr. 19, 2019

(86) PCT No.: PCT/CN2019/083491
§ 371 (c)(1),
(2) Date: Jan. 20, 2022

(87) PCT Pub. No.: WO2020/155415
PCT Pub. Date: Aug. 6, 2020

(65) Prior Publication Data
US 2022/0248960 A1    Aug. 11, 2022

(51) Int. Cl.
*A61B 5/00*    (2006.01)
(52) U.S. Cl.
CPC .......... *A61B 5/0066* (2013.01); *A61B 5/7264* (2013.01)

(58) Field of Classification Search
CPC .................................................. A61B 5/0066
See application file for complete search history.

(56) References Cited

U.S. PATENT DOCUMENTS

2018/0317851 A1    11/2018    Jia et al.
2018/0344149 A1    12/2018    Chong

FOREIGN PATENT DOCUMENTS

| CN | 102764139 A | 11/2012 |
| CN | 102988082 A | 3/2013 |
| CN | 105574861 A | 5/2016 |
| CN | 107452029 A | 12/2017 |
| CN | 108491886 A | 9/2018 |
| CN | 108670239 A | 10/2018 |

*Primary Examiner* — Joseph M Santos Rodriguez
(74) *Attorney, Agent, or Firm* — Bayramoglu Law Offices LLC

(57) ABSTRACT

A three-dimensional (3D) optical coherence tomography angiography (OCTA) method and system based on feature space is provided. OCT signals of scattering samples in a 3D space are acquired by a collector; a theoretical classifier, local signal-noise ratios (SNRs) and decorrelation coefficients of the OCT scattering signals are combined to establish a two-dimensional (2D) feature space to realize classification of dynamic blood flow signals and static tissues. Specifically, computational analysis of first-order and zero-order autocovariance is used to obtain two features of SNR and decorrelation of each OCT scattering signal; a 2D inverse SNR (iSNR)-decorrelation feature (ID) space is established; and based on the multivariate time series theory, a linear classifier is established in the ID space to remove a static surrounding tissue background. The 3D OCTA method and system can improve the contrast of blood flow images and improve the accuracy of blood flow quantification.

6 Claims, 9 Drawing Sheets

THREE-DIMENSIONAL (3D) OPTICAL COHERENCE TOMOGRAPHY ANGIOGRAPHY (OCTA) METHOD AND SYSTEM BASED ON FEATURE SPACE

CROSS REFERENCE TO THE RELATED APPLICATIONS

This application is the national phase entry of International Application No. PCT/CN2019/083491, filed on Apr. 19, 2019, which is based upon and claims priority to Chinese Patent Application No. 201910097827.1, filed on Jan. 31, 2019, the entire contents of which are incorporated herein by reference.

TECHNICAL FIELD

The present invention generally relates to the field of biomedical imaging, and more particularly, to an angiography method associated with optical coherence tomography (OCT) and optical coherence tomography angiography (OCTA), and a blood flow classification method based on a time series model.

BACKGROUND

Blood flow is an important index to measure physiological functions and pathological conditions. At present, common clinical angiography techniques require intravenous injection of exogenous markers, which may cause side effects. Therefore, these angiography techniques are not suitable for long-term and frequent tracking detection of human blood flow and for physical conditions of some patients. In recent years, OCTA, an angiography technique developed based on OCT, uses endogenous blood flow motion to replace the traditional exogenous fluorescent markers. OCTA is non-invasive and marker-free and has the ability to achieve clear and reliable three-dimensional (3D) imaging on a microvascular network in a biological tissue. Therefore, since being invented, the technique has been developed rapidly, and has been used in the research on imaging of fundus, cerebral cortex blood vessel, and skin.

In order to obtain OCTA blood flow images, it is usually necessary to repeat sampling (repeated A-line scan or B-frame scan) in each spatial position of a biological tissue at a specified time interval, a motion intensity at each position is quantified by analyzing the temporal dynamics of OCT scattering signals, and blood flow signals and static tissue signals are classified according to the quantified motion intensities. The reported motion metrics of OCTA are mainly based on the calculation of difference, variance, or decorrelation between adjacent A-line scans (or adjacent B-scan frames). Since the OCTA motion metrics based on decorrelation calculation use the intensity and phase information of signals, classification results are more reliable, and less affected by changes of Doppler angle and overall light source intensity. Moreover, because the decorrelation measures the similarity between adjacent B-scan frames, it is less affected by changes in the overall light source intensity.

However, a motion index of blood flow of OCTA, especially a motion index of a decorrelation coefficient, shows a significant dependence on a noise level of the original OCT scattering signal. As a signal strength attenuates (such as in a deep tissue area), random noise will gradually occupy the main component, and its time-varying characteristics are similar to that of the true blood flow area, thus resulting in decorrelation artifacts. In terms of the motion index of the decorrelation coefficient, it is unable to distinguish the randomness of noise and the decorrelation caused by motion of red blood cells (RBCs). Therefore, an area with low signal-noise ratio (SNR) is easily wrongly determined as a blood flow signal area, which seriously affects a contrast of a blood flow image. As a common solution, an empirical intensity threshold is set to generate an intensity mask to remove all signals with low SNR. However, due to the complex dependency relationship between a decorrelation coefficient and a signal intensity, a simple intensity mask will result in high classification error rate and low motion contrast.

Most of the prior OCTA classification methods lack strong theoretical support, are interfered by the difference between template parameters and actual biological tissues, and cannot effectively achieve the accurate classification of dynamic and static signals; or use complex estimators to correct the influence of SNR on decorrelation, which involves complex calculations and cannot to remove background noise caused by static areas.

SUMMARY

In order to solve the problems in the background art and to overcome the deficiencies of prior arts, the present invention provides a 3D angiography method and system based on OCT in a feature space, where SNR and decorrelation features of OCT signals and a multivariate time series model are used to conduct SNR-adaptive 3D blood flow imaging, which can accurately distinguish between a blood flow and a static area mixed with noise in OCT images.

Objectives of the present invention are achieved through the following technical solutions.

The angiography method includes the following steps: a step of a collector: acquiring OCT scattering signals of scattering signal samples in a 3D space.

a step of a classifier: combining SNRs and decorrelation coefficients of the OCT scattering signals to establish a two-dimensional (2D) feature space to realize classification of dynamic blood flow signals and static tissues and further realize a correction with SNR; and an imaging step: generating an angiography image based on a classification result of the classifier.

The scattering signal samples may be biological tissue samples, and the biological tissue samples may be, for example, human and animal skins, brain tissues, and eyes.

The step of acquiring the OCT scattering signals of the scattering signal samples in the 3D space may specifically include: conducting a 3D OCT scanning on the scattering signal samples and performing a repeated sampling on S different time points in the same spatial position and nearby positions, wherein multiple channels are used for the repeated sampling.

The multiple channels refer to multiple polarization states, multiple scanning incident angles, and the like of light emitted by an OCT light source.

The step of conducting the 3D OCT scanning on the scattering signal samples and performing the repeated sampling on S different time points in the same spatial position and the nearby positions may be achieved through one of the following methods:

a time-domain OCT imaging method of changing an optical path of a reference arm through scanning;

a spectral-domain OCT imaging method of using a spectrometer to record spectral interference signals; and a swept source OCT imaging method of using a swept light source to record the spectral interference signals.

The step of combining the SNRs and the decorrelation coefficients of the OCT scattering signals to establish the 2D inverse SNR and decorrelation coefficient (ID) feature space to realize the classification of the dynamic blood flow signals and the static tissues may specifically include:

S1: using first-order and zero-order autocovariance to conduct computational analysis on the OCT scattering signals, and conducting moving average or Gaussian average in multiple dimensions such as time, space, and channel to obtain two features of SNR and decorrelation coefficient of each OCT scattering signal; and S2: establishing an inverse SNR-decorrelation coefficient feature space, and mapping voxels to the inverse SNR-decorrelation coefficient (ID) feature space; and using a multivariate time series model to establish a linear classifier, and in the inverse SNR and decorrelation coefficient feature space, classifying the OCT scattering signals into dynamic blood flow signals and static tissue noise signals, and using decorrelation coefficients corrected with SNRs to generate the angiography image.

The OCT scattering signals are divided into a dynamic blood flow signal, a noise signal, and a static tissue signal, where the noise signal is a signal of a sample-free area, and the dynamic blood flow signal and the static tissue signal correspond to a blood flow area and a static tissue area, respectively.

S1 may specifically include:

using the first-order and zero-order autocovariance to conduct computational analysis on the OCT scattering signals, and conducting moving average or Gaussian average in multiple dimensions such as 3D space, time, and channel to obtain the two features of the intensity and the decorrelation coefficient of each OCT scattering signal, as shown in FIG. 4A and FIG. 4B.

a feature of the decorrelation coefficient may include: calculating the decorrelation coefficient on an amplitude of an OCT scattering signal obtained from scanning in the same spatial position at S different time points or an OCT scattering signal including an amplitude and a phase to be served as an OCTA blood flow contrast of each OCT scattering signal, i.e., OCTA blood flow information.

In a decorrelation operation, according to a size of a high-dimensional averaging kernel (including the dimensions of time, space, polarization, channel, and the like), a classifier shown in FIG. 4C is established in a feature space; and an angiography image is generated according to a classification result of the classifier, as shown in FIG. 4D.

The multivariate time series model is specifically defined as follows: an acquired OCT scattering signal $X(m,t)$ is obtained from superposition of a backscattering light signal $A(m,t)$ of a biological tissue sample and random noise $n(m, t)$, where m and t refer to a spatial position and a time of a voxel, respectively. Generally, a time series A, n is established under the following conditions: 1. $n(m, t)$ is spatially independent white noise, and is not related to the backscattering light signal $A(m,t)$. 2. $A(m, t)$ is a stable, traverse time series that is spatially independent and identically distributed, which is expected and has a finite variance (second moment). 3. $A(m, t)$ is partially related in time, that is, there is first-order autocovariance, and a value range of a modulus of a first-order autocorrelation coefficient k is [0, 1].

S2 may specifically include: combining the intensities and the decorrelation coefficients of the OCT scattering signals to establish the inverse SNR and decorrelation coefficient (ID) feature space, calculating an asymptotic relationship (formula (5)) between the SNRs and the decorrelation coefficients of the OCT scattering signals through numerical simulation according to the multivariate time series model, and projecting the OCT scattering signals into the inverse SNR and decorrelation coefficient (ID) feature space (as shown in FIG. 4C) to obtain a voxel distribution (formula (6)) in a static area and a noise area, and statistical characteristics (formula (7, 8)) thereof.

In a specific implementation, an asymptotic relationship between the SNRs and the decorrelation coefficients of the OCT scattering signals is calculated through numerical simulation according to the multivariate time series model. In a simulation process, a phase is simulated for the intensity and uniform distribution of A according to the Rayleigh distribution generally recognized, white noise is set as the complex random noise of the Gaussian distribution to generate several simulated images, and an obtained final simulated signal is projected on the SNR-decorrelation coefficient feature space. By calculating a coefficient of variation (CV) of simulated data, according to a model, the variance of decorrelation is inversely proportional to the average parameter, and squared CV of a sample can be fit with the average parameter to obtain a parameter of an inverse proportional function. Furthermore, linear classifier parameters derived from the model are determined by parameters obtained by the simulation and a noise level. In the SNR-decorrelation coefficient feature space, the OCT scattering signals are divided into dynamic blood flow signals and static tissue noise signals. Separated blood flow signals are displayed using a decorrelation value, or directly set to 1 and then displayed.

The classifier for classifying OCT scattering signals in the 2D inverse SNR and decorrelation coefficient feature space (23) may include a direct linear classifier and an improved version thereof. The linear classifier is directly obtained in a 2D feature space through a theoretical formula according to a multi-dimensional averaging kernel size (including a size in space and time, and the number of channels) when an algorithm is executed, and the classifier is universal and is irrelevant to other parameters. The improved classifier refers to a linear classifier obtained by adjusting a slope or an intercept (overall rotation or translation) of the aforementioned linear classifier.

When an angiography image (25) is generated based on a classification result of the classifier, a static tissue signal with a noise signal is removed in the classification result, the remaining signal serves as a dynamic blood flow signal, and a decorrelation coefficient value of the dynamic blood flow signal is used to generate the angiography image, as shown in FIG. 3.

After the angiography image (25) is generated based on the classification result of the classifier, operations such as Gaussian filtering, median filtering, and Hessian filtering are conducted to remove noise to improve the effect of the angiography image.

2. A 3D angiography system based on a feature space includes:

an OCT detection device, configured to acquire OCT scattering signals of scattering signal samples in a 3D space; and one or more signal processors, configured to acquire and analyze intensity information of the OCT scattering signals and OCTA blood flow information, and combine the intensity information of the scattering signals and the OCTA blood flow information to classify dynamic blood flow signals and a static tissue background.

The OCT detection device may include;

a low-coherence light source, an interferometer, and a detector, where the low-coherence light source and the detector are separately connected to the interferometer;

or, a low-coherence light source, an interferometer, and a spectrometer, where the low-coherence light source and the spectrometer are separately connected to the interferometer;

or, a swept wide-spectrum light source, an interferometer, and a detector, where the swept wide-spectrum light source and the detector are separately connected to the interferometer.

A visible light indicating device may be optionally configured in the OCT detection device to indicate a position of an OCT detection beam and guide a placement position of a detection target.

In the method of the present invention, a multivariate time series model is introduced, an OCT signal is described with two features of SNR and decorrelation coefficient (ID), an asymptotic relationship between the two features is established, and it indicates through numerical simulation and theoretical derivation that a variance of an asymptotic distribution is only determined by a high-dimensional averaging kernel size and a local SNR, thereby establishing a simple SNR-adaptive classifier in the ID feature space.

The method of the present invention is based on a multivariate time series model, which supports the effectiveness and feasibility of the proposed classifier. Moreover, compared with other methods, the method of the present invention greatly eliminates the influence of motion artifacts caused by noise.

The present invention has the following beneficial effects and innovations:

Compared with the prior arts, the present invention proposes a theoretical model that describes OCT signals with a multivariate time series and gives an asymptotic relationship between two features (SNR and decorrelation coefficient) of the signals to establish a SNR-adaptive classifier in combination with numerical simulation and theoretical basis. By determining a boundary between blood flow signals that are more in line with the actual signal distribution and other signals, the present invention solves the problem that the prior methods (mainly based on a uniform intensity mask) shows an unsatisfactory inhibition effect on artifacts caused by random noise and improves the quality of blood flow images.

Compared with the prior arts, the present invention has the following significant advantages:

1. For OCTA based on decorrelation calculation, due to the dependency relationship between decorrelation coefficients and SNRs of OCT scattering signals, decorrelation artifacts introduced by random noise in a low SNR area cannot be distinguished from the decorrelation introduced by blood flow motion. Commonly, an empirical threshold is set for intensity masking, that is, an intensity (SNR) threshold is used in the ID feature space to classify blood flow signals and other signals, and the complex dependency relationship between decorrelation coefficients and SNRs of signals makes a boundary between actual blood flow signals and other signals very different from these two straight lines, resulting in a high misclassification rate. Based on the multivariate time series theory, the present invention proposes a mathematical model describing the features of OCT signals and derives an asymptotic relationship between the ID features of the signals; and the present invention gives a formula for calculating the variance of asymptotic distribution through further analysis in combination with numerical simulation, and establishes an SNR-adaptive linear classifier for the ID feature space according to the asymptotic distribution, which can improve the classification accuracy and enable a high blood flow contrast.

2. The effect of traditional intensity masking relies on empirical threshold selection, which lacks a suitable basis. The classifier established by the present invention is determined through a large number of numerical simulation verifications based on a solid theoretical foundation.

3. Decision parameters of the classifier are only determined by the averaging kernel, without any complicated calibration for other parameters of the system. Moreover, a calculation process is extremely efficient, which shows an order-of-magnitude improvement compared to other methods based on machine learning.

3. Compared with the prior methods, the present invention proposes a theoretical basis for establishing the classifier and thus is more reliable. Moreover, since the static and noisy areas are completely removed, the visibility and overall contrast of the angiography image at all SNRs can be improved. According to verification through a large number of samples, the method of the present invention is significantly better than the traditional methods.

BRIEF DESCRIPTION OF THE DRAWINGS

FIG. 4A shows a structure of the blood flow template (intensity) and a curve illustrating the change of the SNR of the template with the depth position;

FIG. 4B shows the decorrelation coefficient of the blood flow template, where the dashed ellipse marks a motion artifact caused by low SNR;

FIG. 4C shows the projection of the voxels of the blood flow template in the inverse SNR and decorrelation coefficient (ID) feature space, where the dark points represent static voxels, the less dark points represent fast-moving dynamic voxels, and the light points represent slow-moving dynamic voxels; in the dashed rectangular box, the solid line represents the asymptotic relationship between SNRs and decorrelation coefficients and the dashed line represents the provided classifier; and the horizontal dashed line represents the traditional intensity threshold classifier, and the dashed ellipse indicates that the proposed method can distinguish more voxel parts than traditional angiography methods;

FIG. 4D shows an angiography image of the proposed method (ID-OCTA) on the blood flow template, where the black dashed line represents a depth that can be imaged by the traditional angiography method on the template;

FIG. 4E is an angiography image of the traditional angiography method (cmOCT) on the blood flow template;

FIG. 4F shows receiver operating characteristic (ROC) curves of the proposed classifier and the traditional intensity threshold classifier, where the curve marked by a diamond is the ROC curve of the proposed classifier and the curve marked by a circle is the ROC curve of the traditional intensity threshold classifier;

where FIG. 5A shows an angiography image of the proposed angiography method (ID-OCTA) on a healthy human skin tissue in vivo;

FIG. 5B shows an angiography image of the traditional intensity threshold method (cmOCT) at a low threshold on a healthy human skin tissue in vivo;

FIG. 5C shows an angiography image of the traditional intensity threshold method (cmOCT) at a high threshold on a healthy human skin tissue in vivo;

FIG. 5D shows magnified images of regions boxed in FIG. 5A and an angiographic cross-sectional view of the proposed angiography method (ID-OCTA) along the dashed line;

FIG. 5E shows magnified images of regions boxed in FIG. 5B and an angiographic cross-sectional view of the traditional intensity threshold method (cmOCT) at a low threshold along the dashed line;

FIG. 5F shows magnified images of regions boxed in FIG. 5C and an angiographic cross-sectional view of the traditional intensity threshold method (cmOCT) at a high threshold along the dashed line;

where FIG. 6A shows a blood vessel area of a healthy human skin tissue in vivo that is manually marked for quantitative analysis, where the light area represents a blood vessel area and the remaining black area represents a background noise area;

where FIG. 6B shows an angiography image of the proposed angiography method (ID-OCTA) on a healthy human skin tissue in vivo;

FIG. 6C shows an angiography image of the traditional intensity threshold method (cmOCT) on a healthy human skin tissue in vivo;

FIG. 6D is a statistical histogram of blood vessel and noise areas in the angiography image of the proposed angiography method (ID-OCTA) on a healthy human skin tissue in vivo;

FIG. 6E is a statistical histogram of blood vessel and noise areas in the angiography image of the traditional intensity threshold method (cmOCT) on a healthy human skin tissue in vivo;

where FIG. 7A is an angiography image of the proposed angiography method (ID-OCTA) with SNR-corrected decorrelation coefficients; and FIG. 7B is an angiography image of the proposed angiography method (ID-OCTA) with uncorrected decorrelation coefficients.

In the figures: 1 represents a collector; 2 represents a classifier; 21 represents the acquisition of OCTA signal features; 22 represents the projection of the OCT scattering signals in the 2D inverse SNR and decorrelation coefficient (ID) feature space; 23 represents the establishment of a classifier to classify the OCT scattering signals in the (ID) feature space, where 231 represents numerical computation of the overall static distribution variance according to formula (5) and 232 represents the establishment of a linear classifier; 24 represents the classification on data according to the established classifier; and 25 represents the generation of an angiography image according to a classification result of the classifier.

DETAILED DESCRIPTION OF THE EMBODIMENTS

Specific implementations of the present invention will be described in detail below in conjunction with the accompanying drawings, and the accompanying drawings constitute a part of the present invention. It should be noted that these descriptions and examples are merely exemplary and cannot be construed as limiting the scope of the present invention. The protection scope of the present invention is defined by the appended claims, and any changes made based on the claims of the present invention are within the protection scope of the present invention.

Examples of the present invention:

In order to facilitate the understanding of the examples of the present invention, operations are described as a plurality of discrete operations, but a description order of operations does not represent an order of implementing the operations.

In the description, the x-y-z 3D coordinate representation based on spatial directions is adopted for the sample measurement space. This description is only used to facilitate discussion, and is not intended to limit the application of the examples of the present invention. The depth z direction is a direction along the incident optical axis; and the x-y plane is a plane perpendicular to the optical axis, where x and y are orthogonal, x represents the OCT transverse fast-scanning direction, and y represents the slow-scanning direction.

The above S, A, n, and the like represent variables, which are only used to facilitate discussion and are not intended to limit the application of the examples of the present invention, and can be any number such as 1, 2, and 3. For the sake of simplicity, the discussion on the multiple channels, polarization states, and other average dimensions of the OCT system is omitted here, and only the space-time dimension is taken as an example. The actual execution steps are the same as the operations in the space-time dimension described below.

Figure 1:
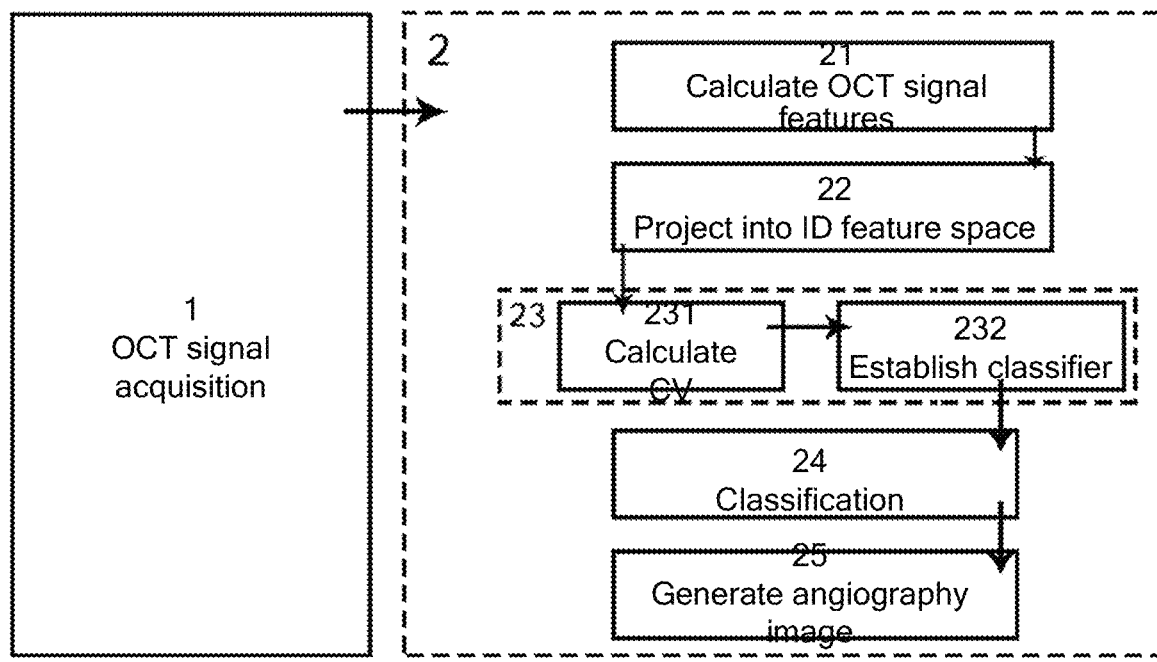
FIG. 1 is a schematic diagram of the method according to the present invention.

The method of the present invention is shown in FIG. 1, including: Signal acquisition: OCT 3D scanning imaging is conducted on a tissue sample, and a repeated sampling is performed in the same spatial position or adjacent spatial positions at T different time points 1. Signal classification: The intensities and decorrelation coefficients of the scattering signals are combined to establish a 2D feature space to realize classification of dynamic blood flow signals and a static tissue background 2.

Specifically:

1) The relative motion between a blood flow and a surrounding tissue is analyzed to obtain the OCTA blood flow ID features (intensity and decorrelation coefficient) of each OCT scattering signal 21.

The decorrelation coefficient is obtained through a decorrelation operation on OCT scattering signals. The decorrelation operation includes computation on complex OCT scattering signals including amplitude and phase obtained from the scanning at S different time points to obtain the decorrelation coefficient. The correlation computation on the complex signals can achieve high motion contrast.

In a specified local area in the blood flow and surrounding tissues, for each voxel, adjacent B-scan frames (x-z plane) of S OCT scans are used for averaging (that is, the high-dimensional averaging kernel is used for convolution) to obtain the first-order and zero-order autocovariance and decorrelation coefficient of each voxel:

$$C = \frac{1}{(S-1)K} \sum_{k=1}^{K} \sum_{s=1}^{S-1} X(m+k, t+s) X^*(m+k, t+s+1) \quad (1)$$

$$I = \frac{1}{SK} \sum_{k=1}^{K} \sum_{s=1}^{S} X(m+k, t+s) X^*(m+k, t+s) \quad (2)$$

$$D = 1 - \frac{|C|}{I} = 1 - \frac{\left| \frac{1}{(S-1)K} \sum_{k=1}^{K} \sum_{s=1}^{S-1} X(m+k, t+s) X^*(m+k, t+s+1) \right|}{\frac{1}{SK} \sum_{k=1}^{K} \sum_{s=1}^{S} X(m+k, t+s) X^*(m+k, t+s)} \quad (3)$$

where C represents the first-order autocovariance and I represents the zero-order autocovariance, as the intensity: D represents the decorrelation coefficient, as the OCTA blood flow information; * represents the conjugate of a complex number, X(m,t) represents a complex signal in a spatial position (z,x) at a time point t; K represents the total number of high-dimensional averaging kernels in the x-y-z space taken when the decorrelation coefficient is calculated; k represents the ordinal number of the high-dimensional averaging kernels in the x-y-z space taken when the decorrelation coefficient is calculated; S represents the total number of the high-dimensional averaging kernels in the time dimension t taken when the decorrelation coefficient is calculated, that is, the number of adjacent B-scan frames in the OCT scan; and s represents the ordinal number of the high-dimensional averaging kernels in the time dimension t taken when the decorrelation coefficient is calculated.

In calculation, the above formula (2) is usually used in combination with the following formula (4) to calculate the intensity feature I (zero-order autocovariance):

$$I = \frac{1}{SK}\sum_{k=1}^{K}\sum_{s=1}^{S} X(m+k, t+s)X^*(m+k, t+s) + X(m+k, t+s)X^*(m+k, t+s+1) \quad (4)$$

In a calculation process, the first and zero-order autocovariance is first calculated with the above formula for each voxel, and averaging is conducted in various dimensions such as time and space to obtain decorrelation values of all voxels in a scan volume of the entire scattering signal sample, which can increase the operational speed.

2) In the OCT system, the noise source is mainly shot noise, which is considered to be approximately constant in the entire scan volume, and can be determined by scanning the air data or calibrating the system in advance.

A local SNR is calculated for each voxel with the following formula, as SNR:

$$SNR = \frac{I}{s^2}$$

where $s^2$ represents a noise level of the OCT system.

The noise level is obtained by calculating an intensity of a data blank area in the OCT scattering signal or calibrating in advance for the OCT system.

3) The SNR detected by the above-mentioned OCT and the OCTA blood flow information obtained based on the decorrelation calculation are combined to establish a 2D SNR-decorrelation coefficient (ID) feature space, and the OCT scattering signal is projected in the feature space 22.

According to results of the time series model, an asymptotic relationship between SNRs and decorrelation coefficients that is expressed by the following formula is obtained, and a 2D inverse SNR and decorrelation coefficient feature space is established;

$$D = 1 - \frac{C}{I} \rightarrow 1 - \rho_1 = 1 - |r| + |r|iSNR \quad (5)$$

where r represents a first-order autocorrelation coefficient of the backscattering light signal A; $\rho_1$ represents a first-order autocorrelation coefficient of the OCT signal X; iSNR represents the inverse SNR; represents convergence; and the number of average voxels is large enough to achieve convergence.

In addition, the decorrelation coefficient D and the intensity I obey the asymptotic normal distribution. In the present invention, noises at various positions of the OCT system are considered to be consistent, and the intensity I and the SNR are in a corresponding relationship. Therefore, there is an asymptotic linear relationship between the inverse SNR and the decorrelation coefficient.

In particular, for static and noise areas, if r=1, $$D \rightarrow iSNR \quad (6)$$

That is, for static and noise voxels, the inverse SNR converges to a decorrelation coefficient. The image area of OCT scattering signals is divided into a blood flow area, a static area, and a noise area.

In particular, for static and noise areas, a variance level of asymptotic distribution is given by simulation calculation, which is only determined by the local SNR and the high-dimensional averaging kernel size N=S×K.

A CV $c_v$ of a decorrelation coefficient of each voxel is calculated using the following formula:

$$c_v^2 = \frac{G}{N}iSNR^2 \quad (7)$$

where $c_v$ represents a CV of a decorrelation coefficient of each voxel; G represents a parameter of an inverse proportional relationship between the squared CV of the decorrelation coefficient and the high-dimensional averaging kernel size; and G≈1.5 is a constant obtained through numerical simulation, which will not be affected by a noise level of the OCT device.

4) A classifier 23 is established to classify the OCT scattering signals in the 2D inverse SNR and decorrelation coefficient feature space 24.

The asymptotic distribution of D is proved to be normal in the time series theory. Generally, a boundary of the asymptotic relationship between the SNR and the decorrelation coefficient is obtained according to the Pauta criterion (3σ principle), and analogous to the microvascular corrosion casting method, the boundary is used as a classifier (that is, the two sides of the boundary are classified into different classes) to remove all static and noise voxels.

A classifier is established to calculate the classification boundary expressed by the following formula:

$$D_c=(1+3c_v)iSNR \quad (8)$$

$D_e$ represents the classification boundary of the decorrelation coefficient in the classifier.

Figure 4A:
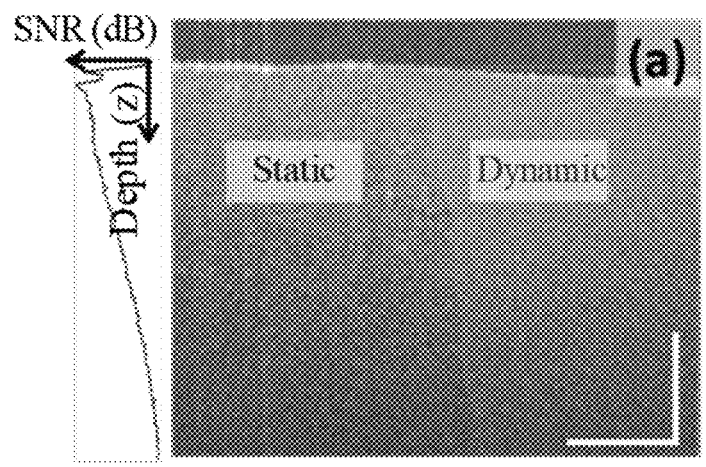
FIGS. 4A-4F show an exemplary result of the present invention on a blood flow template; where

Specifically, as shown in FIG. 4A, when an origin is at the upper left corner, an area above the classification boundary refers to a static tissue with noise, and an area below the classification boundary refers to a dynamic blood flow.

Figure 5A:
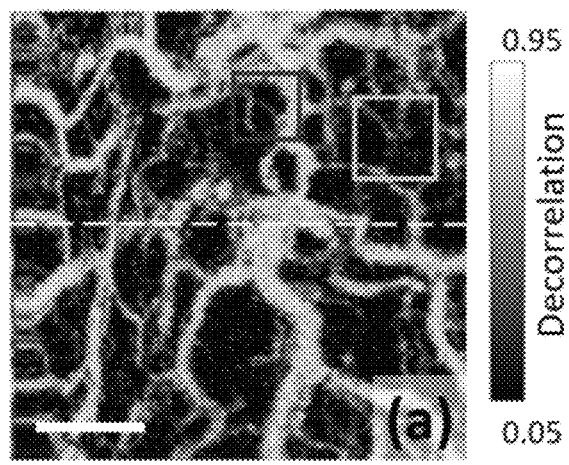
FIGS. 5A-5F show exemplary results of a blood flow imaging experiment on human skin in vivo according to an example of the present invention.

The range can be adjusted according to different requirements of users for classifier performance. Preliminary classification results are processed by morphological filtering or Gaussian filtering from the perspective of graphics to obtain a final OCTA blood flow image, as shown in FIG. 5A.

In addition, according to formula (4), it is known that, for the blood flow area, the decorrelation coefficient changes with the SNR of the signal; and the lower the SNR, the larger the decorrelation coefficient.

5) After classification, the following formula is used to calculate the first-order decorrelation coefficient of the backscattering light signal A(m,t) and replace the decorrelation coefficient, which can eliminate the influence of noise and realize the use of SNR to correct the decorrelation coefficient:

$$D^* = 1 - \frac{1-D}{1-iSNR} \quad (9)$$

where D* represents a first-order decorrelation coefficient obtained after the correction according to SNR.

Figure 7A:
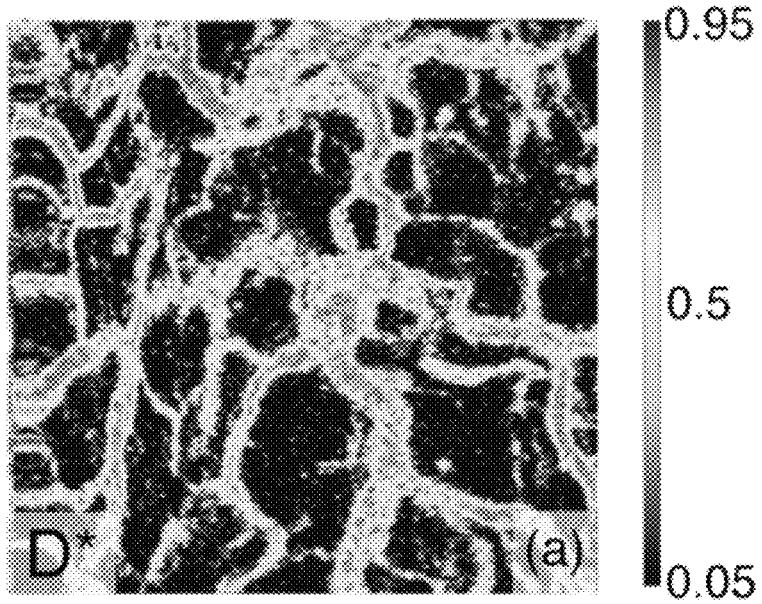
FIGS. 7A-7B show angiography images of the proposed angiography method (ID-OCTA) on a healthy human skin tissue in vivo with SNR-corrected decorrelation coefficients and uncorrected decorrelation coefficients.

According to formula (9), the decorrelation coefficient corrected with SNR is used as a motion metric to eliminate the influence of noise on the motion metric, as shown in FIG. 7A.

Compared with the traditional decorrelation coefficient, the present invention uses the decorrelation coefficient corrected with SNR as a motion metric according to formula (9) to eliminate the influence of noise on the motion metric, which can better remove the influence of noise and truly reflect the intensity of blood flow that changes over time. The contrast effect with the uncorrected decorrelation coefficient is shown in FIG. 7.

Figure 2:
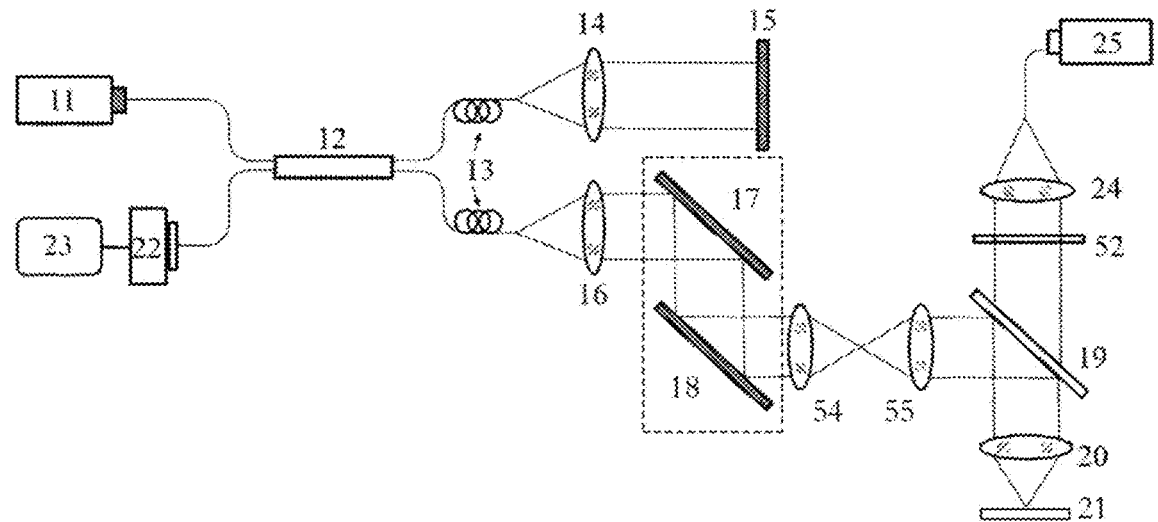
FIG. 2 is a schematic diagram of the device according to the present invention.

FIG. 2 is a schematic structure diagram of the collector of the OCT angiography technique based on the ID feature space in the present invention. A main structure of the low-coherence interferometry part of the device is an interferometer composed of 11 to 23. A light source 11 is connected to an input end at a side of a beam splitter 12, and light emitted by the light source 11 is divided into two light beams by the beam splitter 12: one of the light beams enters a reference arm of the interferometer through a polarization controller 13 and is irradiated on a reference plane mirror 15 through a reference arm collimation lens 14; and another one of the light beams enters a sample arm through another polarization controller 13, and is specifically focused on a sample 21 to be tested through a collimation lens 16 and an optical path of a scanning device. In an optical path of the scanning device, a light beam is reflected by the 2D scanning galvanometer group 17 and 18, the "4f" lens group 54 and 55, and the dichroic mirror 19, and then is focused on the sample 21 to be tested through an objective lens 20. The lens group 54 and 55 is composed of two lenses 54 and 55 arranged on the same optical axis. The lens group 54 and 55 is designed to ensure that a beam center of the 2D scanning galvanometer surface and a beam center of the dichroic mirror reflection surface are fixed during scanning, such that the beam in the OCT sample arm does not affect the imaging properties of the objective lens during scanning.

Then, the light reflected by each of the reference arm and the sample arm returns to the beam splitter 12 and output through the original path, and is received by an interference signal detection device 22 after interference. The interference signal detection device 22 is connected to a signal processor module and calculation unit 23. For a fiber optical path, two polarization controllers 13 are used to adjust a polarization state of a light beam to maximize the signal interference effect.

In a specific implementation, a visible light indicating device is also provided. The visible light indicating device includes a low-power visible light source 25, a collimation lens 24, and an optical filter 52. Visible light for indication passes through the collimation lens 24, the optical filter 52, the dichroic mirror 19, and the focusing objective lens 20 in sequence and then reaches the sample 21 to be tested.

According to different ways of detecting signals through low-coherence interference, the 3D blood flow imaging system based on a feature space shown in FIG. 2 specifically includes:

1) A time-domain detection device The light source 11 adopts broadband low-coherence light, the plane mirror 15 can move along the optical axis direction, and the interference signal detection device 22 is a point detector. The plane mirror 15 is moved to change an optical path of the reference arm, and interference signals of the two arms are detected by the point detector 22, such as to achieve the low-coherence interference detection of scattering signals in the z direction of a specific spatial depth and thus obtain a sampling volume in the depth spatial dimension.

2) A spectral-domain detection device The light source 11 adopts broadband low-coherence light, the plane mirror 15 is fixed, and the interference signal detection device 22 is a spectrometer. When an interference signal passes through a line scan camera in the spectrometer 22, an interference spectrum is recorded. The Fourier analysis method is used to analyze the interference spectrum signal, and the scattering information in the depth z direction is acquired in parallel, such as to obtain a sampling volume in the depth spatial dimension.

3) A swept detection device The light source 11 adopts a swept light source, the plane mirror 15 is fixed, and the interference signal detection device 22 is a point detector. The point detector 22 records the low-coherence interference spectra of the swept light source in a time-division manner. The Fourier analysis method is used to analyze the interference spectrum signal, and the scattering information in the depth z direction is acquired in parallel, such as to obtain a sampling volume in the depth spatial dimension.

Each of the different detection devices mentioned above can be used according to the OCT scanning imaging method involved in the description of FIG. 1 to analyze a relative motion between a blood flow and a surrounding tissue to generate an OCTA image, and conduct graphic filtering on the OCTA image to obtain an enhanced OCTA image.

Figure 3:
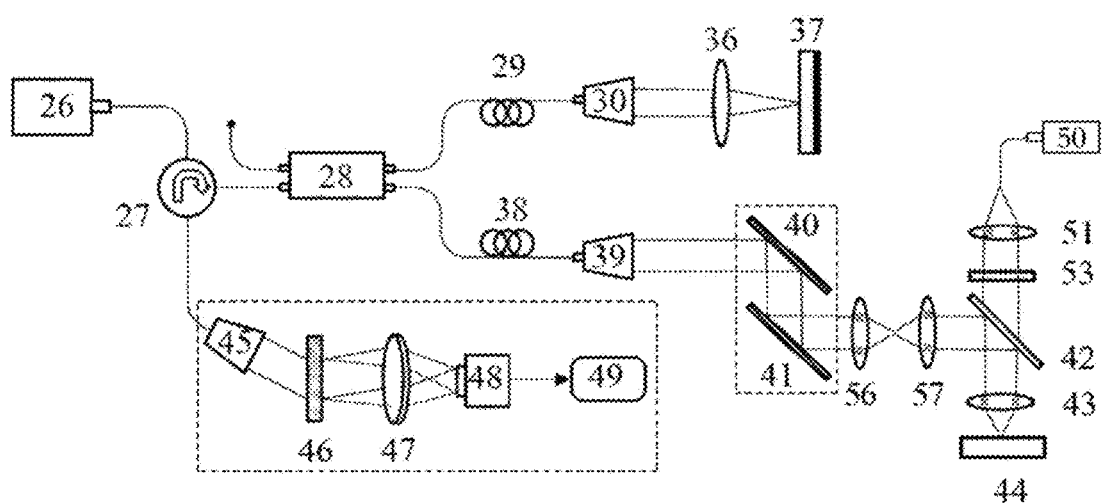
FIG. 3 is a schematic diagram of the device according to an example of the present invention.

FIG. 3 shows an exemplary use example of the present invention. The 3D OCT angiography system based on an ID feature space includes a broadband low-coherence light source 26, an optical circulator 27, a fiber coupler 28 with a splitting ratio of 50:50, a first polarization controller 29, a first fiber collimation device 30, a focusing lens 36, a plane mirror 37, a second polarization controller 38, a second fiber collimation device 39, a 2D scanning galvanometer group 40 and 41, a dichroic mirror 42, a focusing objective lens 43, a third fiber collimation device 45, a grating 46, a focusing lens 47, a high-speed line scan camera 48, a signal processor module and calculation unit 49, a visible light indicating light source 50, a collimation lens 51, and a "4f" lens group 56 and 57.

The broadband low-coherence light source 26 shown in this example is a super-luminescent diode light source with a center wavelength of 1,325 nm and a bandwidth of 100 nm. The focusing objective lens 43 is an achromatic doublet with a focal length of 30 mm. The high-speed line scan camera 48 is a line scan camera composed of 2,048 pixel units. Light emitted by the low-coherence broadband light source 26 used in this exemplary device passes through the optical circulator 27 and then enters an input end at a side of the fiber coupler 28 with a splitting ratio of 50:50, and light emitted from the fiber coupler 28 is divided into two sub-beams: one of the sub-beams passes through the first polarization controller 29 and reaches the first fiber collimation device 30 in the reference arm via an optical fiber, and then the sub-beam passes through the collimation lens and the focusing lens 36 and then is irradiated on the plane mirror 37; and the other one of the sub-beams passes through the second polarization controller 38 and reaches the second fiber collimation device 39 of the sample arm via an optical fiber, and then the sub-beam is collimated, reflected by the two scanning galvanometers 40 and 41, the "4f" lens group 56 and 57, and the dichroic mirror 42, and then focused on the sample 44 to be tested by the focusing objective lens 43 and scattered through back reflection. The lens group 56 and 57 is designed to ensure that a beam center of the 2D scanning galvanometer surface and a beam center of the dichroic mirror reflection surface are fixed during scanning. The light reflected by the plane mirror 37 in the reference arm interferes with the backscattering light of the sample to be tested in the sample arm at the fiber coupler 28, and interference light is detected and recorded by the spectrometer 4548, and then acquired, analyzed, and processed as a single by the signal processor module and calculation unit 49. The spectrometer includes devices 45 to 48 connected in sequence, where the device 45 is a fiber coupler, the device 46 is a grating, and the device 47 is a converging lens, which focuses light separated through grating dispersion on a linear array detector shown in 48.

In a specific implementation, a visible light indicating device is also provided. The visible light indicating device includes a visible light indicating light source 50 and a collimation lens 51. Visible light for indication emitted by the visible light indicating light source 50 passes through the collimation lens 51, the dichroic mirror 42, and the focusing objective lens 43 and then reaches the sample 44 to be tested.

Figure 4B:
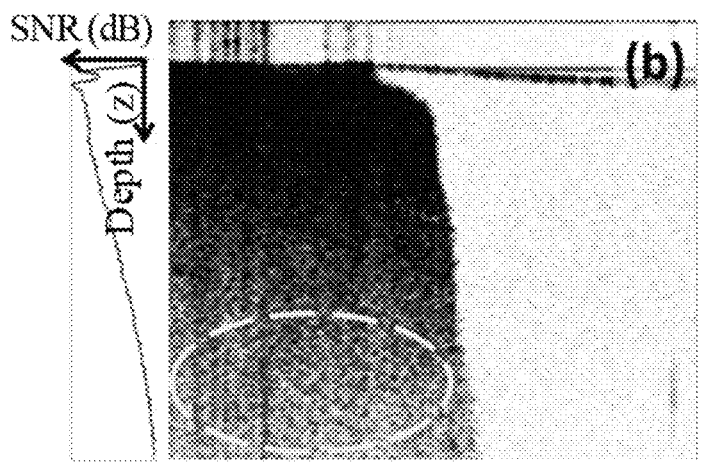
Figure 4C:
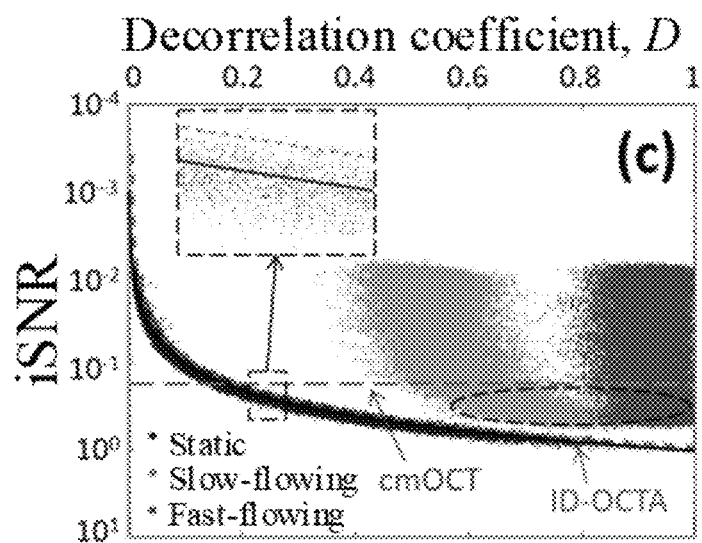
Figure 4D:
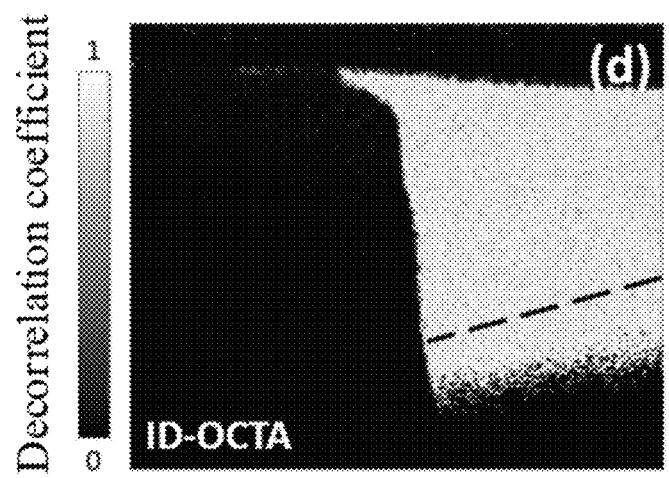
Figure 4E:
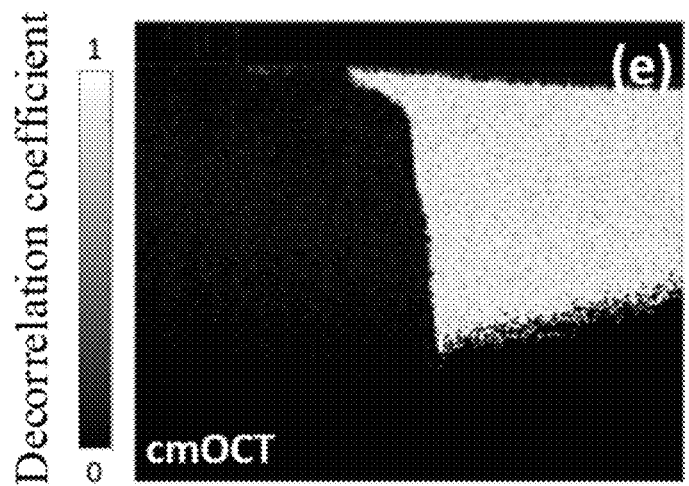
Figure 4F:
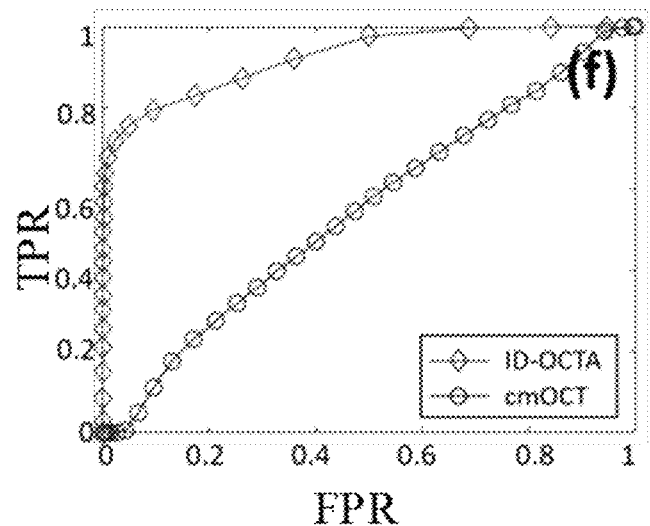

FIGS. 4A-4F show an experimental result on a blood flow template (simulated) obtained in this example. FIG. 4A and FIG. 4B correspond to a representative cross-sectional OCT structure diagram and OCTA image of the simulated template, respectively. FIG. 4A shows the static, dynamic, and noise signal areas. The classification characteristics of a known signal such as imaging data of the simulated template can facilitate quantification of the classification effect. FIG. 4C shows the projection of the static, dynamic, and noise signals in the inverse SNR and decorrelation coefficient (ID) feature space, and obviously, there is a clear distinction between dynamic signals and static signals. The proposed ID classifier and the traditional uniform intensity threshold are each applied to the ID feature space to distinguish blood flow signals and tissue noise signals, and classification results in FIG. 4D and FIG. 4E are obtained, respectively. The accuracy of blood flow signal classification is quantified through a true positive rate (TPR) and a false positive rate (FPR), and an advantage of the blood flow classification method of establishing a classifier based on machine learning over the traditional method is quantitatively evaluated. The TPR is defined as a ratio of the number of pixels classified into true blood flow signals among blood flow signals to the number of all pixels classified into blood flow signals. The higher the TPR, the more accurate the classification. The FPR is defined as a ratio of the number of pixels of noise signals classified into blood flow signals to the number of pixels of all noise signals. The lower the FPR, the fewer false positive samples obtained by the classifier. Therefore, the higher the TPR and the lower the FPR, the better the classifier, such that the distinction between dynamic signals and static signals is more obvious and a blood flow image with higher contrast can be obtained. It can be seen from the figure that the proposed ID feature classifier can image a deeper area under the same FPR than the traditional method, and the difference in depth between the two can be clearly indicated by the black dashed line. With these two indexes as two coordinate axes, ROC curves are plotted. When the TPR is 80%, the ID-OCTA method only has a TPR of 9.9%, but the traditional intensity threshold method has a TPR up to 75.7%.

Figure 5B:
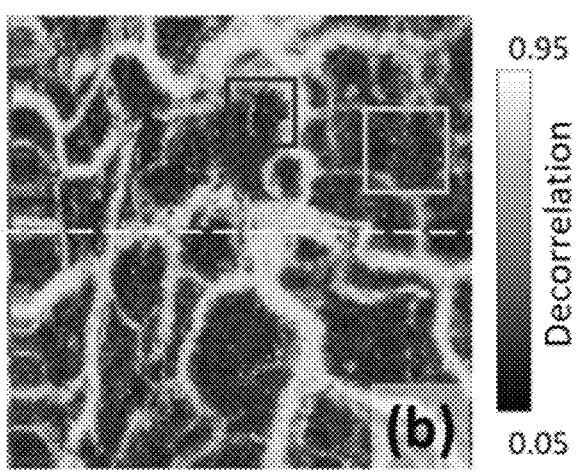
Figure 5C:
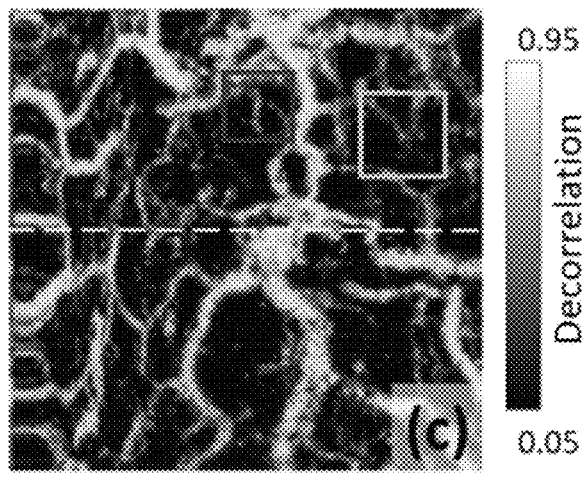
Figure 5D:
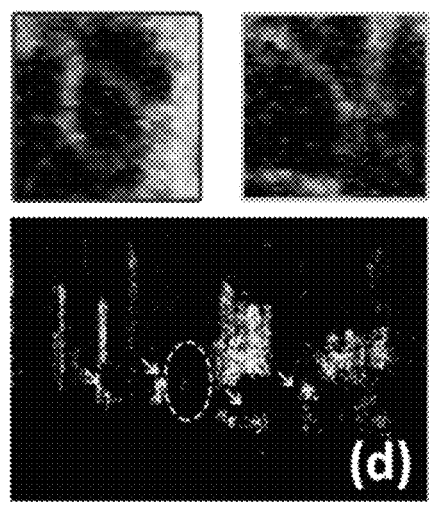
Figure 5E:
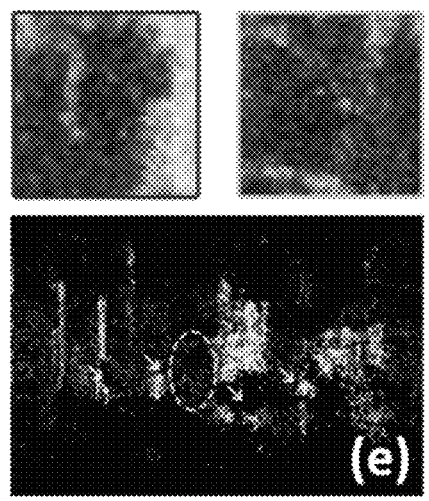
Figure 5F:
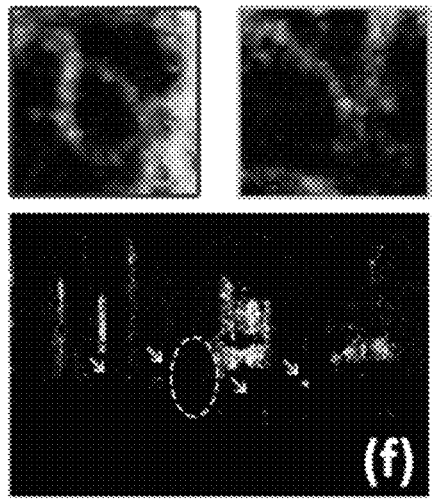

In addition, a 3D angiography experiment is conducted on a normal healthy human skin area in vivo. FIGS. 5A-5F show the angiography results of this example on human skin in vivo. FIG. 5A shows an angiography image of the proposed ID-OCTA method, and FIG. 5B shows an angiography image of the traditional intensity threshold method, where a threshold is set to be approximately twice a noise level of the system. In contrast, the superficial large blood vessels can be clearly observed in the two methods due to high blood flow velocity and large decorrelation coefficient. However, the traditional intensity threshold cannot lead to the elimination of a large number of static areas, resulting in a high background noise level in the angiography image. This makes it difficult to see the tiny capillaries. As shown in the area selected by the box and an enlarged detailed view thereof, the background filled with noise reduces the visibility of some capillaries. FIG. 5C shows a result at an increased intensity threshold. By increasing the intensity threshold to about six times the noise level, the background noise of an obtained angiography image can be inhibited to a level similar to that of the proposed ID-OCTA method. However, obviously, a lot of blood vessel areas with low SNR are also excluded. Through comparison of frontal vascular projection images, it can be seen that the low intensity threshold method causes many static signals to be misclassified as blood flow signals and retained, which weakens a contrast of tiny capillaries; and the high intensity threshold method falsely excludes a large number of blood vessels with low SNR concentrated in deep areas. FIG. 5D, FIG. 5E, and FIG. 5F are angiographic cross-sectional views of FIG. 5A, FIG. 5B, and FIG. 5C, respectively, where arrows are used to point out the comparison of some details. In contrast, in FIG. 4F, the blood vessels at the yellow arrow are falsely removed as noise by the high intensity threshold; and as shown in FIG. 5E, a large number of noise areas are falsely retained by the low intensity threshold. Therefore, through the comparison of the in vivo imaging results shown in FIG. 5, it can be seen that the visibility of tiny capillaries is significantly enhanced in the angiography image obtained by the method provided by the present invention, and thus the contrast of the entire angiography image is significantly improved.

Figure 6A:
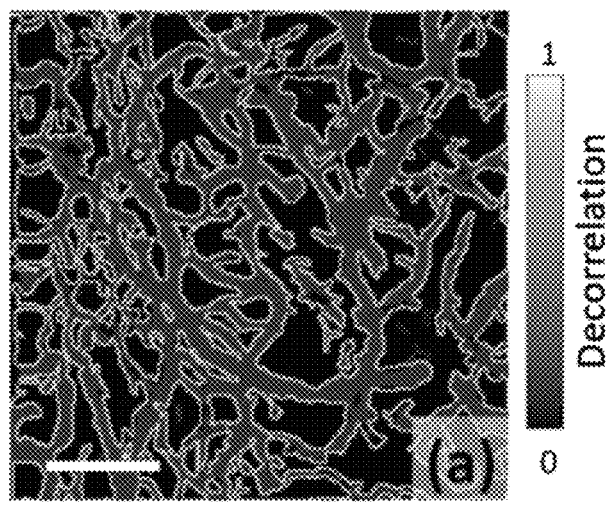
FIGS. 6A-6E show the quantitative analysis and comparison of the present invention and the traditional method.
Figure 6B:
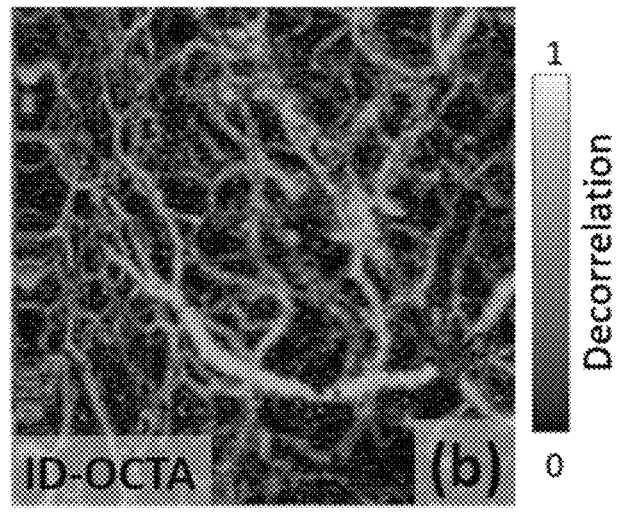
Figure 6C:
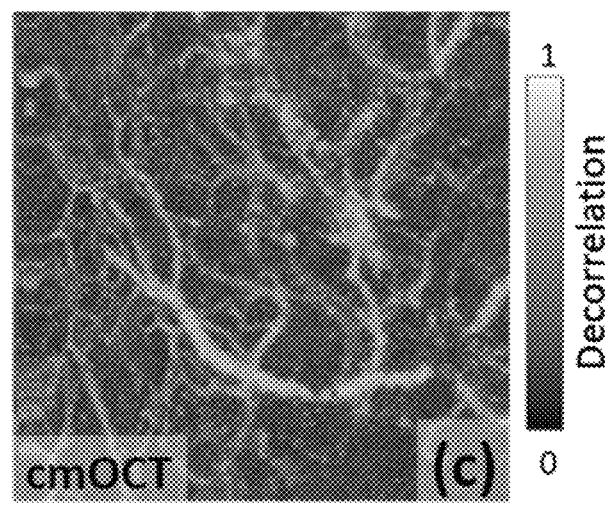
Figure 6D:
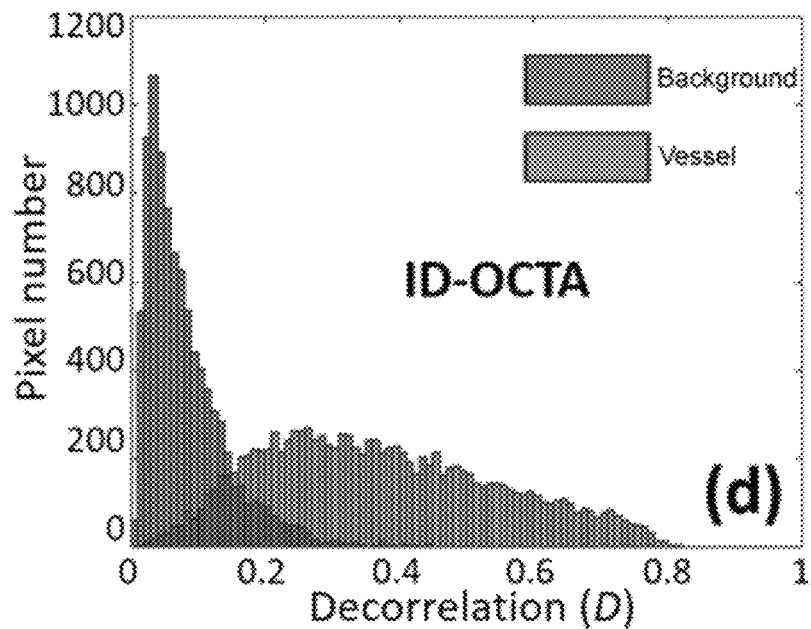
Figure 6E:
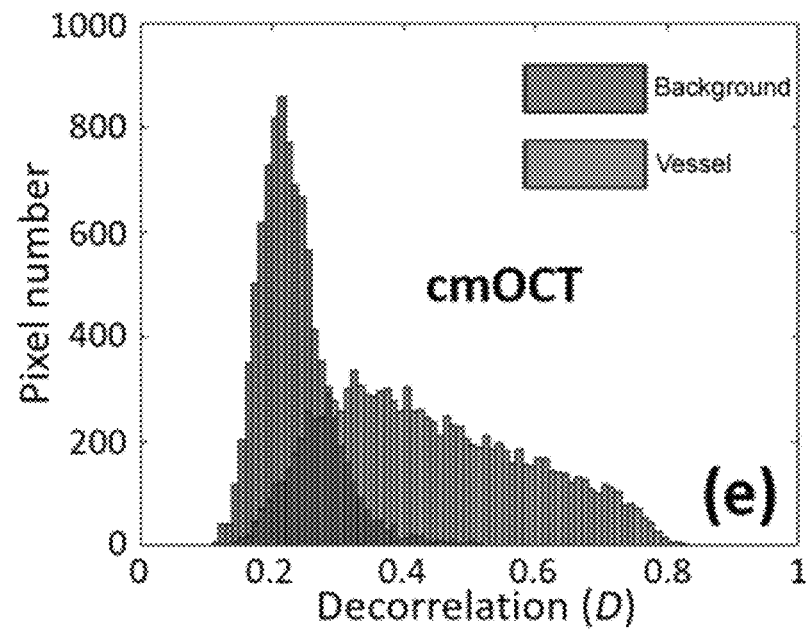

Further, in order to quantify the contrast improvement brought by the proposed ID-OCTA method, the present invention uses the contrast-noise-ratio (CNR) to measure the improvement of the proposed algorithm. As shown in FIG. 6A, the blood vessel area and the background noise area are marked in the frontal vascular projection images of the ID-OCTA method and the traditional method. It can be seen from FIG. 6B and FIG. 6C that the background of the traditional threshold method is significantly noisier. FIG. 6D and FIG. 6E are statistical histograms of blood vessel areas and background noise areas, which further confirm the contrast improvement of the proposed method. The CNR is calculated by the following formula.

$$CNR = \frac{\overline{D_s} - \overline{D_n}}{\sigma_n}$$

where $\overline{D_s}, \overline{D_n}$ represent mean values of decorrelation coefficients for the blood vessel areas and the background noise areas, respectively; and $\sigma_n$ represents a standard deviation (SD) for the background noise areas. According to a test on 6 different samples and the paired data t-test, the CNR (5.96±1.00) of ID-OCTA is significantly higher than that (5.03±0.89) of the traditional threshold method, with a significance level of $5.75*10^{-4}$, which shows that the proposed method truely enhances a contrast of an angiography result.

Figure 7B:
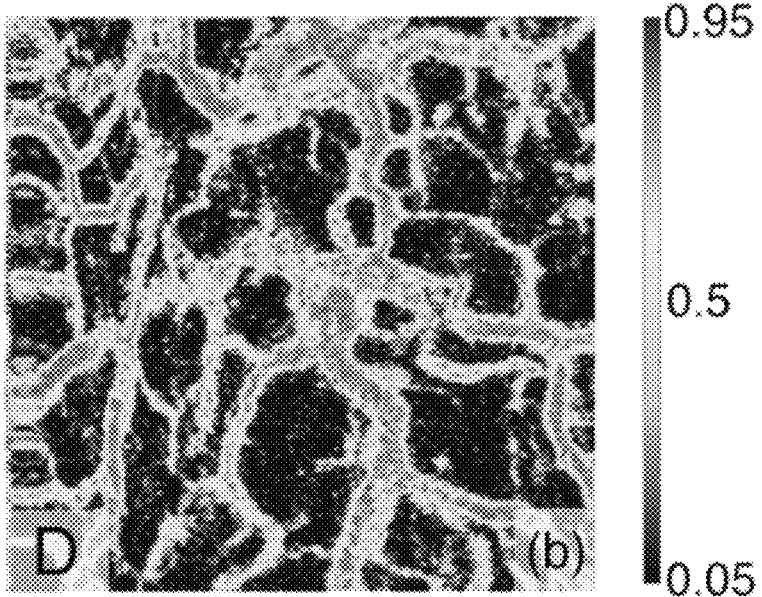

FIGS. 7A-7B show the angiography result of SNR-corrected decorrelation coefficients, and compared with uncorrected decorrelation coefficients, the residual noise can be corrected more thoroughly and thus the contrast of the angiography image can be further improved. Moreover, the method of the present invention can lead to a truer motion contrast for areas with low SNR (such as deep blood vessels) compared with the traditional method, which helps users to make a correct interpretation of results and also facilitates the subsequent hemodynamic quantification work. The above experimental comparison results fully indicate that the 3D angiography method based on a feature space involved in the present invention can improve the accuracy of blood flow signal classification, can achieve the effective enhancement of blood flow contrast and the improvement of angiography image quality, and has an outstanding technical effect.

What is claimed is:

1. A three-dimensional (3D) optical coherence tomography angiography (OCTA) method based on feature space, comprising: a step of a collector: acquiring OCT scattering signals from samples in a 3D space; a step of a classifier: combining signal-noise ratios (SNRs) and decorrelation coefficients of the OCT scattering signals to establish a two-dimensional (2D) feature space to realize classification of dynamic blood flow signals and static tissues and further realize a correction with SNR; and an angiography step: generating angiography images based on a classification result of the classifier;

wherein the step of combining the SNRs and the decorrelation coefficients of the OCT scattering signals to establish the 2D feature space to realize the classification of the dynamic blood flow signals and the static tissues specifically comprises:

S1: using first-order and zero-order autocovariance to conduct computational analysis on the OCT scattering signals, and conducting moving average or Gaussian average in multiple dimensions comprising time, space, and channel to obtain two features of SNR and decorrelation coefficient of each OCT scattering signal; and S2: establishing an SNR-decorrelation coefficient feature space, and mapping voxels to an inverse SNR and decorrelation coefficient (ID) feature space; and using a multivariate time series model to establish a linear classifier, and in an inverse SNR and decorrelation feature space, classifying the OCT scattering signals into dynamic blood flow signals and static tissue noise signals, and using decorrelation coefficients corrected with SNRs to generate the angiography image;

S2 specifically comprises:

A) combining the inverse SNR detected by the OCT and the decorrelation coefficient based on the decorrelation calculation to establish a 2D inverse SNR-decorrelation feature (ID) space, and projecting the OCT scattering signals in the ID space: according to results of the multivariate time series model, obtaining an asymptotic relationship between inverse SNRs and decorrelation coefficients that is expressed by the following formula, and establishing a 2D inverse SNR and decorrelation coefficient feature space:

$$D = 1 - \frac{C}{I} \to 1 - \rho_1 = 1 - |r| + |r|iSNR$$

wherein r represents a first-order autocorrelation coefficient of a backscattering light signal A: an OCT scattering signal X(m,t) is obtained from superposition of the backscattering light signal A(m,t) of a biological tissue sample and random noise n (m,t), wherein m and t refer to a spatial position and a time of a voxel, respectively; $\rho_1$ represents a first-order autocorrelation coefficient of the OCT signal X; iSNR represents the inverse SNR; $\to$ represents convergence; C represents a first-order autocovariance; I represents a zero-order autocovariance, as an intensity D represents a decorrelation coefficient;

for a static area and a noise area, when r=1, $$D \to iSNR \quad (6)$$

that is, for static and noise voxels, the inverse SNR converges to the decorrelation coefficient;

B) establishing a classifier to classify the OCT scattering signals in the 2D inverse SNR and decorrelation coefficient feature space: establishing a classifier to calculate a classification boundary expressed by the following formula:

$$D_c = (1+3c_v)iSNR$$

$D_c$ represents the classification boundary of the decorrelation coefficient in the classifier, and $c_v$ represents a coefficient of variation (CV) of a decorrelation coefficient of each voxel.

2. The 3D OCTA method based on the feature space according to claim 1, wherein the step of acquiring OCT scattering signals from samples in a 3D space specifically comprises: conducting OCT scanning on the 3D scattering signal samples and performing a repeated sampling on S different time points in a same spatial position and nearby positions, wherein multiple channels are used for the repeated sampling, and S represents the number of adjacent B-scan frames in the OCT scan.

3. The 3D OCTA method based on the feature space according to claim 2, wherein the step of conducting the OCT scanning on the 3D samples and performing the repeated sampling on S different time points in the same spatial position and the nearby positions is achieved through one of the following methods: a time-domain OCT imaging method of changing an optical path of a reference arm through scanning; a spectral-domain OCT imaging method of using a spectrometer to record spectral interference signals; and a swept source OCT imaging method of using a swept light source to record the spectral interference signals.

4. The 3D OCTA method based on the feature space according to claim 1, wherein S1 specifically comprises: using the first-order and zero-order autocovariance to conduct computational analysis on the OCT scattering signals, and conducting moving average or Gaussian average in multiple dimensions comprising 3D space, time, and channel to obtain the two features of the SNR and the decorrelation coefficient of each OCT scattering signal.

5. The 3D OCTA method based on the feature space according to claim 1, wherein a feature of the decorrelation coefficient comprises: calculating the decorrelation coefficient on an amplitude of an OCT scattering signal obtained from scanning in the same spatial position at S different time points, or an OCT scattering signal comprising amplitude and phase parts to be served as an optical coherence tomography angiography (OCTA) blood flow contrast of each OCT scattering signal, i.e., OCTA blood flow information, wherein S represents the number of adjacent B-scan frames in the OCT scan.

6. The 3D OCTA method based on the feature space according to claim 1, wherein S2 specifically comprises: combining the SNRs and the decorrelation coefficients of the OCT scattering signals to establish the inverse SNR and decorrelation coefficient feature space, calculating an asymptotic relationship between the inverse SNRs and the decorrelation coefficients of the OCT scattering signals through numerical simulation according to the multivariate time series model, and projecting the OCT scattering signals into the inverse SNR and decorrelation coefficient feature space to obtain a voxel distribution in the static area and the noise area, and statistical characteristics of the voxel distribution.

* * * * *